(12) United States Patent
Haase

(10) Patent No.: US 9,974,901 B2
(45) Date of Patent: May 22, 2018

(54) DRUG INFUSION SYSTEM AND METHOD

(71) Applicant: Medtronic, Inc., Minneapolis, MN (US)

(72) Inventor: James M. Haase, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 903 days.

(21) Appl. No.: 14/301,909

(22) Filed: Jun. 11, 2014

(65) Prior Publication Data

US 2015/0359963 A1 Dec. 17, 2015

(51) Int. Cl.
A61M 1/00 (2006.01)
A61M 5/142 (2006.01)
A61M 5/145 (2006.01)

(52) U.S. Cl.
CPC ...... A61M 5/14276 (2013.01); A61M 5/1452 (2013.01)

(58) Field of Classification Search
CPC .................. A61M 5/14276; A61M 5/1452
USPC ....................................................... 604/151
See application file for complete search history.

(56) References Cited

U.S. PATENT DOCUMENTS

| 6,770,067 | B2 | 8/2004 | Lorenzen et al. |
| 7,341,577 | B2 | 3/2008 | Gill |
| 7,798,789 | B2 | 9/2010 | Haase et al. |
| 8,162,874 | B2 | 4/2012 | Whitehead et al. |
| 8,262,616 | B2 | 9/2012 | Grant et al. |
| 8,939,737 | B2 | 1/2015 | Gray |
| 2006/0056998 | A1 | 3/2006 | Gray et al. |
| 2008/0286132 | A1* | 11/2008 | Haase ............... A61M 5/14216 417/413.1 |

* cited by examiner

Primary Examiner — Jason Flick
(74) Attorney, Agent, or Firm — W. Schmidt, Esq.; Medtronic, Inc.

(57) ABSTRACT

An actuator for an infusion drive mechanism comprises a piston defining a first axis and being movable within a passageway of the infusion drive mechanism to convey at least one infusion medium. The passageway defines a longitudinal axis. An armature is connected to the piston and defines at least one cavity configured for disposal of a biasing member engageable with a surface of the infusion drive mechanism to orient the first axis transverse relative to the longitudinal axis. Systems and methods of use are disclosed.

7 Claims, 3 Drawing Sheets

DRUG INFUSION SYSTEM AND METHOD

TECHNICAL FIELD

The present disclosure generally relates to medication infusion systems and methods and, more particularly to a drug infusion pump having a drive configuration that provides a consistent delivery of infusion media.

BACKGROUND

Medication infusion devices may be used to deliver an infusion media to a subject. Such devices may be implanted to deliver dosages of the infusion media to a selected location in the subject's body, for example, in the vessels, spinal column and/or peritoneal cavity. For example, medication pump devices can include a drive mechanism that includes a reciprocating actuator having a piston and an armature. In some cases, the pump device has a solenoid coil that can be alternately energized and de-energized to reciprocate the piston within a piston chamber between a forward stroke to deliver infusion media to the subject and a return stroke to refill the piston chamber with infusion media.

Pump orientation and/or gravity effects on a pump device can alter the clearances between the piston and piston chamber, affecting the delivery rate of the infusion media. Over time, reciprocal motion of the actuator can result in wear of pump components, which can effect pump performance. Pump orientation and/or gravity effects may also contribute to wear. This disclosure describes an improvement over these prior art technologies.

SUMMARY

In one embodiment, an actuator for an infusion drive mechanism is provided. The actuator comprises a piston defining a first axis and being movable within a passageway of the infusion drive mechanism to convey at least one infusion medium. The passageway defines a longitudinal axis. An armature is connected to the piston and defines at least one cavity configured for disposal of a biasing member engageable with a surface of the infusion drive mechanism to orient the first axis transverse relative to the longitudinal axis. In some embodiments, systems and methods are provided.

BRIEF DESCRIPTION OF THE DRAWINGS

The present disclosure will become more readily apparent from the specific description accompanied by the following drawings, in which.

DETAILED DESCRIPTION

Figure 1:
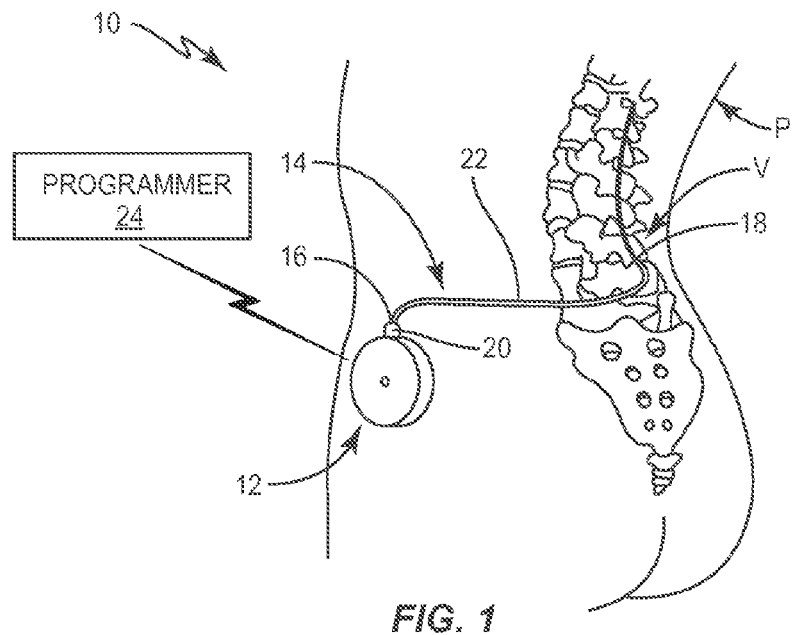
FIG. 1 is a perspective view of components of one embodiment of a system in accordance with the principles of the present disclosure disposed with a subject.

The exemplary embodiments of medication infusion systems and methods disclosed are discussed in terms of medical devices for therapeutic treatment of a subject, and more particularly to a drug infusion pump having a drive configuration that provides consistent delivery of infusion media. In some embodiments, the present system comprises an infusion system and/or a process that employ a drive configuration having an actuator configured for efficient operation for conveying a variety of types of infusion media to facilitate consistent stroke delivery. In some embodiments, the drive configuration reduces wear of its constituent components.

In one embodiment, the present infusion system includes a drug pump that is configured to convey infusion media at an infusion rate that is independent of an orientation of the pump. In one embodiment, the present infusion system includes a drug pump that is configured to convey infusion media at an infusion rate that is independent of the force of gravity on an actuator of the pump. In some embodiments, the actuator is disposed with the pump to resist and/or prevent non-desirable friction and clearance effects from a change of orientation, orientation sensitivity and/or due to gravity forces on the actuator. In one embodiment, orientation sensitivity of the actuator is reduced by altering the ratio of length vs. diameter (L/D) of a piston of the actuator.

In one embodiment, a piston return spring of the pump is disposed adjacent to and non-concentric with the piston and piston bore. In one embodiment, disposal of the piston return spring adjacent to and non-concentric with the piston and piston bore provides a greater L/D relative to an actuator including a pole/piston configuration that comprises a spring located in a counter bore of a cylinder of a magnetic cup subassembly and concentric with the piston. In some embodiments, a greater L/D reduces wear of one or more components of the drive configuration. In one embodiment, disposal of the piston return spring adjacent to and non-concentric with the piston and piston bore provides a side load on the piston to stabilize clearances of the piston with the piston bore under multiple orientations of the actuator.

In one embodiment, the pump includes one or more biasing members, such as, for example, coil springs disposed with pockets located on an underside of a pump actuator pole, such as, for example, a side facing a coil of the pump. In one embodiment, one end of a spring is disposed against the pole, and the other side of the spring is disposed against a titanium barrier covering the coil. In one embodiment, a spring is biased to one side of a piston bore axis to provide a slight off-center load, which creates a moment holding the piston tilted to one side of the piston bore. In some embodiments, this configuration provides a consistent fluidic resistance and friction characteristic of the actuator, which creates a consistent back leakage for infusion media conveyance and piston speed. In some embodiments, this configuration provides a consistent stroke volume in all orientations of the actuator. In some embodiments, this configuration provides localized wear of one or more components of the pump such that wear is more consistently located adjacent a larger and/or maximum side load. For example, this configuration can provide localized wear adjacent sides of a piston and a bore where the off-center load is at a maximum.

In one embodiment, the pump includes an increase in a supported length of the piston thereby reducing back leakage for infusion media conveyance. In some embodiments, this configuration guides the piston in the piston bore. In some embodiments, this configuration facilitates stroke delivery by providing a consistent stroke and reduces wear.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". The system and methods of the present disclosure may also be used on animals, bone models and other non-living substrates, such as, for example, in training, testing and demonstration.

As used in the specification and including the appended claims, "treating" or "treatment" of a disease or condition refers to performing a procedure that may include administering one or more drugs to a subject (human patient, normal or otherwise, or other mammal), employing implantable devices, and/or employing instruments that treat a disease in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. Also, as used in the specification and including the appended claims, the term "tissue" includes soft tissue, muscle, ligaments, tendons, cartilage and/or bone unless specifically referred to otherwise.

The following discussion includes a description of a medication infusion system and related methods of employing the medication infusion system in accordance with the principles of the present disclosure. Alternate embodiments are also disclosed. Reference is made in detail to the exemplary embodiments of the present disclosure, which are illustrated in the accompanying figures. Turning to FIGS. 1-5, there are illustrated components of a medication infusion system 10, which comprises an implantable infusion device 12.

The components of implantable infusion device 12 can be fabricated from biologically acceptable materials suitable for medical applications, including metals, synthetic polymers, ceramics and/or their composites. For example, the components of implantable infusion device 12, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics, thermoplastics such as polysulfone, polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, or any combination thereof.

Various components of implantable infusion device 12 may have material composites, including the above materials, to achieve various desired characteristics such as strength, rigidity, elasticity, compliance, biomechanical performance, durability and radiolucency or imaging preference. The components of implantable infusion device 12, individually or collectively, may also be fabricated from a heterogeneous material such as a combination of two or more of the above-described materials. The components of implantable infusion device 12 may be monolithically formed, integrally connected or include fastening elements and/or instruments, as described herein.

Implantable infusion device 12, as shown in FIG. 1, is configured to be surgically implanted into a subject patient P, for example, in the abdominal region, between skin and an abdominal wall. A catheter 14, which is connected to implantable infusion device 12, is configured to deliver one or more infusion media, as described herein, to patient P, for example, by conveying an infusion medium to a selected location in a venous system, adjacent a spinal column, or adjacent a peritoneal cavity of patient P. In some embodiments, implantable infusion device 12 may be implemented as external infusion device that connects to patients through catheter devices. In some embodiments, catheter 14 may comprise a plurality of catheter segments. In some embodiments, catheter 14 may be a unitary catheter. Catheter 14 is positioned such that one or more fluid delivery outlets of catheter 14 are proximate to the one or more target sites within patient P. In some embodiments, multiple catheters 14 may be coupled to implantable infusion device 12 to target the same or different tissue or nerve sites within patient P. In some embodiments, implantable infusion device 12 may include a plurality of reservoirs for storing more than one infusion media.

An end 16 of catheter 14 is coupled to implantable infusion device 12, while an end 18 of catheter 14 is located proximate to the target site. In some embodiments, implantable infusion device 12 includes a catheter connection port 20 connected to tubing 22 to deliver infusion media to patient P. In some embodiments, implantable infusion device 12 includes a refill port and a reservoir for disposal of infusion media. In some embodiments, implantable infusion device 12 includes a power source (not shown), which may include a rechargeable battery, non-rechargeable battery, traditional battery and/or an external transcutaneous inductive power supply.

In some embodiments, catheter 14 is placed in an intrathecal space and conveys infusion medium into spinal fluid surrounding a spinal cord of vertebrae V. Implantable infusion device 12 can be configured for intrathecal drug delivery into the intrathecal space, as well as epidural delivery into the epidural space, both of which surround the spinal cord. In some embodiments, the epidural space (also known as "extradural space" or "peridural space") is the space within the spinal canal (formed by vertebrae V) lying outside the dura mater, which encloses the arachnoid mater, subarachnoid space, the cerebrospinal fluid, and the spinal cord. In some embodiments, the intrathecal space is within the subarachnoid space of the spinal cord, which is past the epidural space and dura mater and through the theca of the spinal cord. In some embodiments, implantable infusion device 12 may be implemented to administer infusion medium into neurological tissue, such as, for example, brain tissue.

In some embodiments, medication infusion system 10 can include a target delivery site for infusion media within patient P adjacent sacral nerves, a pudendal nerve, a perineal nerve or other areas of the nervous system, and/or to manage peripheral neuropathy or post-operative pain mitigation, ilioinguinal nerve therapy, intercostal nerve therapy, gastric stimulation for the treatment of gastric motility disorders and/or obesity, muscle stimulation, for mitigation of other peripheral and localized pain, for example, leg pain or back pain. In some embodiments, catheter 14 may be positioned to deliver infusion media to a deep brain site or within a heart, for example, intraventricular delivery. In some embodiments, delivery of infusion media within the brain may help manage disorders including depression or other mood disorders, dementia, obsessive-compulsive disorder, migraines, obesity, and movement disorders, such as Parkinson's disease, spasticity, and epilepsy.

In some embodiments, the one or more infusion media can comprise a therapeutic substance, which can include a substance intended to have a therapeutic effect on the patient, e.g., pharmaceutical compositions, genetic materials and/or biologics. In some embodiments, the pharmaceutical compositions may include chemical formulations intended to have a therapeutic effect such as intrathecal antispasmodics, insulin, pain medications, chemotherapeutic agents, anti-inflammatory agent, anticoagulants, antibiotics, nutritional fluids, gene therapy agent and/or baclofens. In some embodiments, the pharmaceutical compositions can be configured to function effectively in an implanted environment by possessing various characteristics including stability at body temperature to retain therapeutic qualities and/or concentration to reduce the frequency of replenishment.

In some embodiments, the genetic materials may include substances intended to have a direct or indirect genetic therapeutic effect such as genetic vectors, genetic regulator elements, genetic structural elements and/or DNA. In some embodiments, the biologics may include substances that are living matter, or derived from living matter, and offer a therapeutic effect to the patient such as stem cells, platelets, hormones and/or biologically produced chemicals.

In some embodiments, the one or more infusion mediums can comprise saline solutions and/or fluoroscopy agents. In some embodiments, implantable infusion device 12 can deliver one or more infusion mediums to patient P according to one or more dosing programs that set forth different therapy parameters, such as a therapy schedule specifying programmed doses, dose rates for the programmed doses, and specific times to deliver the programmed doses. In some embodiments, the dosing programs may be a part of a program group for therapy, where the group includes a plurality of dosing programs and/or therapy schedules. In some embodiments, implantable infusion device 12 may be configured to deliver infusion media to patient P according to different therapy schedules on a selective basis. In some embodiments, implantable infusion device 12 may include a memory to store one or more therapy programs, instructions defining the extent to which patient P may adjust therapy parameters, switch between dosing programs, or undertake other therapy adjustments.

Medication infusion system 10 includes an external programmer 24, which wirelessly communicates with implantable infusion device 12 as needed, such as to provide or retrieve therapy information or control aspects of therapy delivery (for example, modify therapy parameters, on/off, infusion rate). In some embodiments, patient P and/or a practitioner may select and/or generate additional dosing programs for use by implantable infusion device 12 via external programmer 24.

In some embodiments, programmer 24 may be a handheld computing device that includes a display, such as, for example, a screen, a liquid crystal display or a light emitting diode display and a user input, such as, for example, a keypad, buttons, a peripheral pointing device, touch screen and/or voice recognition. In some embodiments, programmer 24 may include and/or comprise a component of a workstation, cellular phone, personal computer, laptop, notebook and/or tablet. In some embodiments, programmer 24 may transmit information to and/or from implantable infusion device 12, such as, for example, catheter type, catheter position, volume of therapeutic agent(s) delivered, refill interval, baseline orientation and/or therapy parameters. In some embodiments, programmer 24 may transmit information to and/or from implantable infusion device 12, such as, for example, dosing program information, such as dose amount, rate of delivery, a time interval between successive supplemental boluses and/or maximum dose.

In some embodiments, programmer 24 may communicate with implantable infusion device 12 and/or other computing devices via wireless communication, such as, for example, using radio frequency (RF) telemetry, local wireless communication, such as RF communication according to the 802.11 or Bluetooth specification sets, infrared (IR) communication according to the IRDA specification set, or other standard or proprietary telemetry protocols, wired communication, and/or via exchange of removable media, such as magnetic or optical disks, or memory cards or sticks, and/or via a local area network, wide area network, public switched telephone network, or cellular telephone network. In some embodiments, implantable infusion device 12 may include one or more processors, which may comprise programmer 24. Such processors may include one or more microprocessors, digital signal processors, application specific integrated circuits, field programmable gate arrays and/or programmable logic circuitry. In some embodiments, implantable infusion device 12 may include memory to store information, as described herein, associated with the one or more processors, such as, for example, volatile or non-volatile media, such as a random access memory (RAM), read only memory (ROM), non-volatile RAM, electrically erasable programmable ROM and/or flash memory.

In some embodiments, implantable infusion device 12 has an outer housing that is constructed of a biocompatible material that resists corrosion and degradation from bodily fluids, such as titanium or biologically inert polymers. Implantable infusion device 12 may be implanted within a subcutaneous pocket close to the therapy delivery site. For example, implantable infusion device 12 is implanted within an abdomen of patient P. In some embodiments, implantable infusion device 12 includes a modular medical pump that facilitates assembly of at least a portion of the pump components separately from the pump housing (or bulkhead) of implantable infusion device 12 containing a fluid, a fluid reservoir, a port and a medical pump subassembly.

Figure 2:
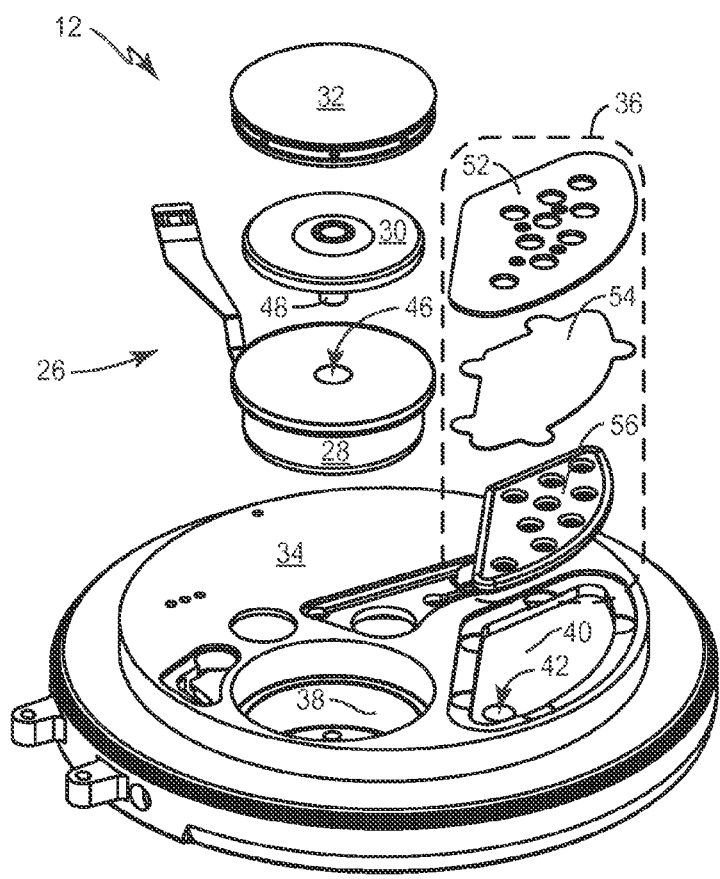
FIG. 2 is a perspective view of components of one embodiment of a system in accordance with the principles of the present disclosure with parts separated.

Implantable infusion device 12 includes a medical pump 26 that includes a modular pump coil 28, an actuator, such as, for example, a piston/pole assembly 30 and a cover 32, as shown in FIG. 2. Implantable infusion device 12 also includes a bulkhead 34 and a filter 36. Bulkhead 34 includes a cup-mounting bay 38 to receive modular pump coil assembly 28 and a filter-mounting bay 40 to receive filter 36. A fluid passageway 42 connects cup-mounting bay 38 to filter-mounting bay 40.

Figure 3:
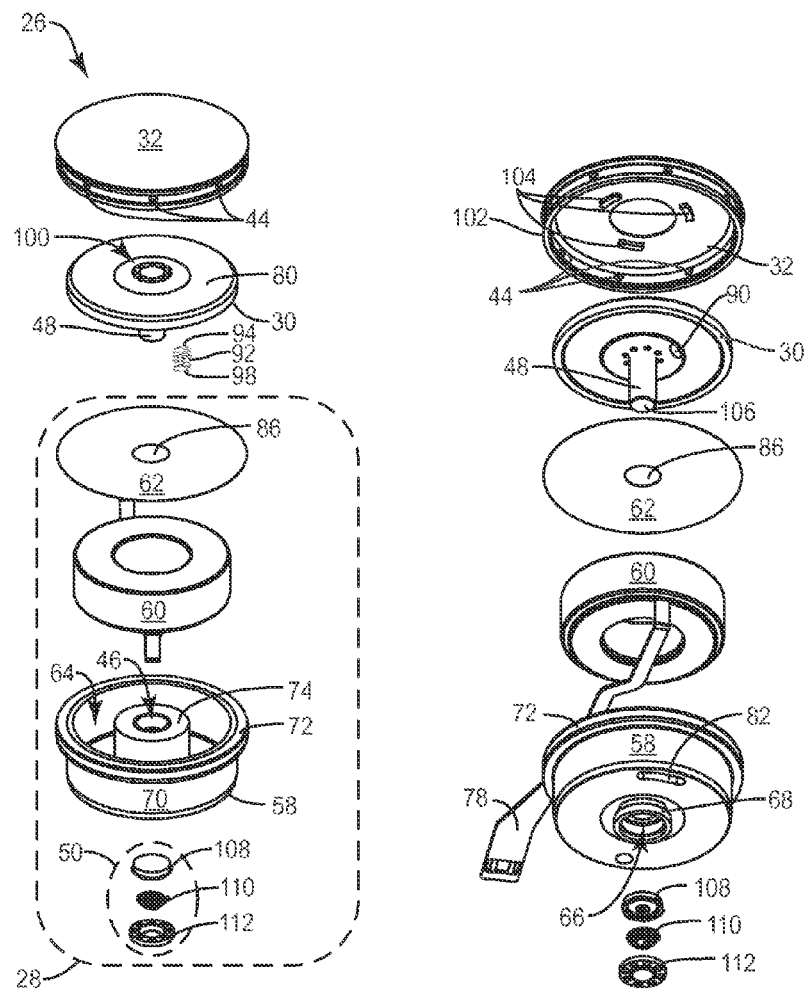
FIG. 3 is a perspective view of components of one embodiment of a system in accordance with the principles of the present disclosure with parts separated.
Figure 5:
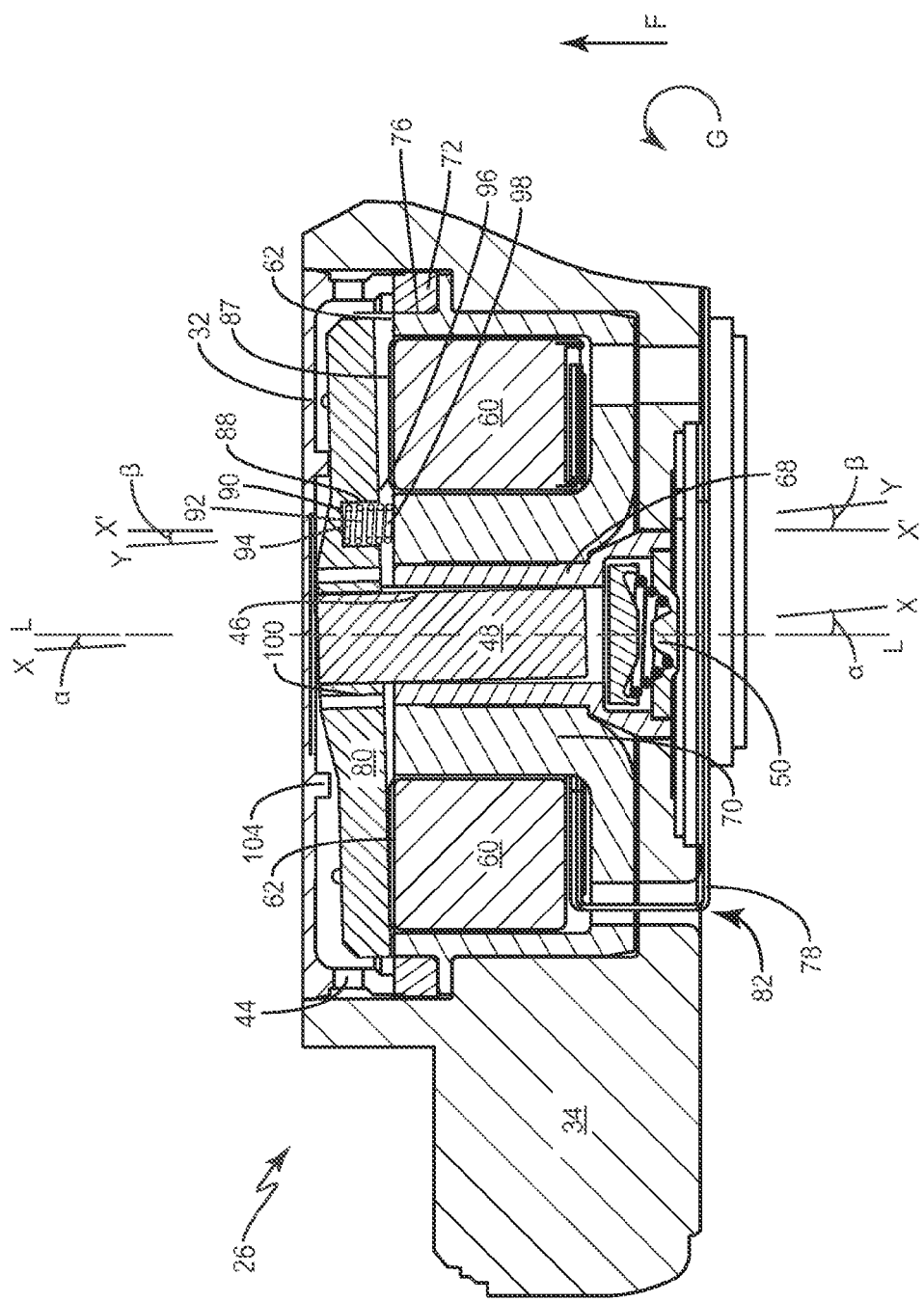
FIG. 5 is a side cross section view of components of one embodiment of a system in accordance with the principles of the present disclosure.

During operation of medical pump 26, infusion media flows through filter 36 and into cup-mounting bay 38 via fluid passageway 42. Within cup-mounting bay 38, the infusion media enters an enclosure including piston/pole assembly 30 through holes 44 in cover 32, as shown in FIG. 3. Once within the enclosure under cover 32, the infusion media enters a passageway, such as, for example, a central aperture 46 and is forced by the motion of a piston 48 through a one-way valve 50. Central aperture 46 defines a longitudinal axis L, as shown in FIG. 5. After passing through valve 50, the infusion media is directed to one or more target sites within a patient, as described herein.

Filter 36 includes a filter cover 52, a filter element 54 and a filter base 56, as shown in FIG. 2. Base 56 forms a seal with filter-mounting bay 40 to prevent infusion media from bypassing filter element 54 prior to entering fluid passageway 42. Filter cover 52 compresses filter element 54 and base 56 to provide a seal between filter element 54 and base 56, as well as a seal between base 56 and bulkhead 34. Filter cover 52 may be attached to bulkhead 34 by interference fit and/or screws (not shown). In some embodiments each of the elements of filter 36 comprise corrosion-resistant materials. In some embodiments, base 56 comprises a deformable material, such as a polymer or silicone rubber. In some embodiments, base 56 comprises stainless steel. In some embodiments, cover 52 comprises a polymer or stainless steel.

Figure 4:
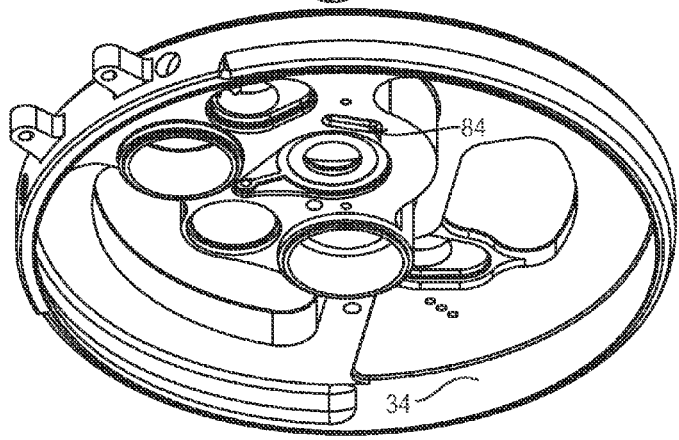
FIG. 4 is a perspective view of components of one embodiment of a system in accordance with the principles of the present disclosure with parts separated.

Pump coil assembly 28 operates to drive piston/pole assembly 30 during a pump stroke of medical pump 26. Pump 26 employs electromagnetic and mechanical forces to translate piston/pole assembly 30 between a retracted position or return stroke and a forward position or pump stroke to cause infusion medium to be drawn into central aperture 46 and forced out of central aperture 46 to one or more target sites within patient P. Pump coil assembly 28 includes a coil assembly 58, an electromagnetic coil 60, a barrier plate 62 and one-way valve 50, as shown in FIGS. 3-5. Electromagnetic coil 60 fits underneath barrier plate 62 and within a recess 64 of coil assembly 58. One-way valve 50 seals against a seat 66 within the end of a sleeve 68 of coil assembly 58 opposite barrier plate 62.

Coil assembly 58 includes a magnetic coil housing 70, a weld ring 72 and sleeve 68. Magnetic coil housing 70 forms recess 64. Within recess 64, magnetic coil housing 70 includes a protrusion 74. Magnetic coil housing 70 forms central aperture 46 in protrusion 74, which receives sleeve 68. In some embodiments, sleeve 68 is interference fit within central aperture 46 and/or secured within central aperture 46.

Weld ring 72 surrounds recess 64 and fits within a groove 76 of magnetic coil housing 70. In some embodiments, weld ring 72 is interference fit to groove 76 of magnetic coil housing 70 and/or secured therewith. In some embodiments, magnetic coil housing 70 comprises a highly magnetic material. The highly magnetic material of magnetic coil housing 70 efficiently magnetizes in response to current through electromagnetic coil 60. In some embodiments, magnetic coil housing 70 may comprise a highly magnetic steel alloy. In some embodiments, magnetic coil housing 70 may comprise a highly magnetic stainless steel alloy such as 430F. Magnetic coil housing 70 is separated from the flow path of fluid being pumped by medical pump 26 to prevent corrosion of magnetic coil housing 70. As discussed herein, weld ring 72 combines with bulkhead 34, barrier plate 62 and sleeve 68 to separate magnetic coil housing 70 from the flow path.

Electromagnetic coil 60 comprises one or more insulated conductors arranged in a multitude of turns. In some embodiments, electromagnetic coil 60 comprises a single continuous conductor or more than one conductor electrically connected in series or in parallel. Electromagnetic coil 60 includes flex circuit 78, which provides the electrical connections used to deliver current to electromagnetic coil 60. Delivering current to electromagnetic coil 60 magnetizes magnetic coil housing 70 to attract a pole 80 for a pump stroke of medical pump 26. Flex circuit 78 fits through a hole 82 of magnetic coil housing 70 and through a hole 84 of bulkhead 34, as shown in FIG. 4. Hole 84 is formed in the bottom of cup-mounting bay 38 and is aligned with hole 82 to receive flex circuit 78.

Barrier plate 62 covers recess 64 to enclose electromagnetic coil 60 within recess 64. Barrier plate 62 forms a mating aperture 86, which provides an inner diameter of barrier plate 62. Mating aperture 86 is aligned with central aperture 46 of magnetic coil housing 70. The inner diameter of barrier plate 62 is sealed to sleeve 68, whereas the outer diameter of barrier plate 62 is sealed to weld ring 72. As such, the inner diameter of barrier plate 62 may be smaller than the inner diameter of magnetic coil housing 70, but larger than the inner diameter of sleeve 68. Barrier plate 62 comprises a relatively thin material to provide magnetic performance for pump 26 while maintaining sufficient strength and stiffness to isolate electromagnetic coil 60 and magnetic coil housing 70 from the flow path. In some embodiments, barrier plate 62 may have a thickness between about 0.0005 inches to about 0.10 inches. In some embodiments, barrier plate 62 may have a thickness between about 0.001 inches to about 0.010 inches, a thickness between about 0.001 inches to about 0.005 inches, a thickness of less than about 0.010 inches, a thickness of less than about 0.005 inches, a thickness between about 0.00175 inches to about 0.00225 inches, or a thickness of about 0.002 inches.

Piston/pole assembly 30 includes piston 48 and pole 80. Piston/pole assembly 30 is positioned such that piston 48 is located within central aperture 46 of modular pump coil assembly 28. Piston 48 defines an axis X, as shown in FIG. 5, and extends through central aperture 46 in connection with pole 80, positioned adjacent to an open side 87 of magnetic coil housing 70. Pole 80 includes an inner surface 88 that defines a cavity, such as, for example, a cylindrical pocket 90 configured for disposal of a biasing member, such as, for example, a coil spring 92, which is disposed adjacent to and non-concentric with piston 48 and central aperture 46. Spring 92 includes an end 94 that engages inner surface 88 and pocket 90 defines an opening face 96 such that an end 98 of spring 92 engages barrier plate 62, which covers and/or engages magnetic coil housing 70 and/or coil 60. This configuration applies a side load to piston 48 to stabilize clearances of piston 48 with central aperture 46 under multiple orientations of piston/pole assembly 30 with and/or relative to pump 26, implantable infusion device 12 and/or a patient's body, as described herein.

Pocket 90 defines an axis Y, which is spaced and offset from axis X and axis L. Spring 92 engages the surfaces of pole 80 and barrier plate 62 such that piston 48 is oriented transverse relative to central aperture 46, and axis X is oriented transverse relative to axis L. Engagement of spring 92 with the surfaces of pole 80 and barrier plate 62, which may engage magnetic coil housing 70 and/or coil 60, applies a force, in the direction shown by arrow F in FIG. 5, to pole 80, which rotates piston/pole assembly 30, in the direction shown by arrow G, thereby biasing piston 48 to one side of axis L to provide an off-center load, which creates a moment holding piston 48 tilted to one side of central aperture 46. As such, piston 48 is substantially fixedly disposed with central aperture 46 such that axis X is oriented relative to axis L at an angle α.

In some embodiments, pump 26 comprises a diametric clearance between piston 48 and central aperture 46 of a particular dimension and/or value in a range of approximately 6-16 microns and an engagement length of piston 48 in central aperture 46 of approximately 5000 microns such that angle α can be disposed at a particular angle in a range of approximately 0.07 to 0.18 degrees. In some embodiments, pump 26 comprises a diametric clearance between piston 48 and central aperture 46 of a particular dimension and/or value in a range of approximately 3-25 microns and an engagement length of piston 48 in central aperture 46 of approximately 5000 microns such that angle α can be disposed at a particular angle in a range of approximately 0.03 to 0.28 degrees.

In some embodiments, the off-center load stabilizes piston 48 such that the clearance between piston 48 and the walls of central aperture 46 does not change under multiple orientations of piston/pole assembly 30, pump 26 and/or implantable infusion device 12. As such, piston 48 is reciprocally movable within central aperture 46 substantially independent of the orientation of pump 26. In some embodiments, this configuration provides a consistent fluidic resistance and/or friction characteristic of piston/pole assembly 30, which creates a consistent back leakage for infusion media conveyance and piston speed. In some embodiments, this configuration provides a consistent stroke volume in all orientations of piston/pole assembly 30.

Pocket 90 is disposed with pole 80 such that pocket 90 and spring 92 disposed therein, are positioned in a non-concentric orientation with piston 48. As such, axis Y is disposed in a non-concentric orientation with axis X. In one embodiment, this configuration provides a supported length of piston 48 and/or an increased L/D to reduce back leakage for infusion media conveyance. In some embodiments, this configuration guides piston 48 in central aperture 46. In some embodiments, this configuration facilitates stroke delivery by providing a consistent stroke and reduces wear.

Spring 92 imparts a spring force between pole 80 and magnetic coil housing 70 to urge piston/pole assembly 30 toward its retracted position, as described herein. In some embodiments, spring 92 is movably disposed with pocket 90 such that axis Y is oriented relative to an axis X', disposed substantially parallel to axis X, and/or axis L at an angle β. In some embodiments, angle β can be disposed at a particular angle in an angular range, similar to the ranges described with regard to angle α. In some embodiments, angle α is equal to angle β. In some embodiments, angle α and angle β are different. In some embodiments, axis Y is disposed at alternate orientations, relative to axis X and/or axis L, such as, for example, parallel, transverse, perpendicular and/or other angular orientations such as acute or obtuse, and/or may be offset or staggered. In one embodiment, one end of spring 92 is disposed against pole 80, and the other side of spring 92 is disposed against a titanium barrier plate 62 covering coil 60. In some embodiments, spring 92 is made of a biocompatible and infusion medium compatible material that exhibits a spring force such as, for example, titanium, stainless steel and/or MP35N cobalt steel.

In one embodiment, pole 80 includes an inner surface that defines a plurality of cavities, such as, for example, a plurality of cylindrical pockets, each pocket similar to pocket 90 described herein and configured for disposal of a biasing member, as described herein, and each pocket being disposed adjacent to and non-concentric with piston 48 and central aperture 46. In one embodiment, pump 26 includes one or more biasing members, as described herein disposed with pockets located on an underside of a pump actuator pole, such as, for example, pole 80, which includes a side facing coil. In some embodiments, the biasing member may include one or more of an elastomeric member, clip and/or leaf spring.

Spring 92 biases piston/pole assembly 30 away from modular pump coil assembly 28 such that pole 80 is spaced apart from barrier plate 62. In some embodiments, piston 48 may be interference fit to pole 80 and/or secured to pole 80. Pole 80 comprises a magnetic material that is attracted to coil assembly 58 to produce a pump stroke, as described herein. In some embodiments, pole 80 comprises stainless steel. Between holes 44 formed in cover 32 and central aperture 46, infusion media flows through holes 100 in piston 48 as well as through a gap between pole 80 and an inner surface of a sidewall 102 of cover 32. Because pole 80 is within the fluid flow path, the material of pole 80 resists corrosion. In some embodiments, pole 80 comprises a magnetic stainless steel alloy, such as AL29-4. Piston 48 is located within the fluid flow path and resists corrosion. In some embodiments, piston 48 comprises sapphire material, which can limit wear between piston 48 and sleeve 68 caused by the pumping action of medical pump 26. In some embodiments, piston 48 comprises cobalt-chromium-molybdenum (Co—Cr—Mo) material, which can limit wear. In some embodiments, piston 48 comprises a metal material, such as a stainless steel or titanium alloy. In some embodiments, piston/pole assembly 30 comprises a unitary component consisting of a single magnetic material such as a stainless steel alloy.

Cover 32 mounts to barrier plate 62 to form an enclosure containing piston/pole assembly 30 and spring 92. When medical pump 26 is assembled, cover 32 is secured to bulkhead 34 within cup-mounting bay 38. In some embodiments, cover 32 may be interference fit within cup-mounting bay 38 and/or secured to bulkhead 34 using a weld joint and/or one or more screws. Cover 32 includes holes 44, which allow the infusion media passing through medical pump 26 to enter the enclosure formed by cover 32 after passing through fluid passageway 42.

Cover 32 includes protrusions 104, which are located on its interior surface adjacent to pole 80. Protrusions 104 constrain the motion of piston/pole assembly 30 thereby limiting the maximum stroke length of a pump stoke. As such, the height of protrusions 104 may be selected to set the stroke length of a pump stroke. As the volume of infusion media delivered by medical pump 26 per pump stroke directly (pump-stroke volume) relates to the stroke length, medical pump 26 facilitates different pump-stroke volumes by changing the height of protrusions 104. In some embodiments, the other components of medical pump 26 can be identical for different pump-stroke volumes. In some embodiments, the pump-stroke volume depends on the diameter of piston 48 and the inner diameter of sleeve 68, and can be selected in combination with a stroke length to provide selected pump-stroke volumes.

In use, system 10 including implantable infusion device 12, similar to the systems, devices and methods described herein, is implanted within the body of patient P, as shown in FIG. 1. Implantable infusion device 12 can be utilized for a wide variety of therapies including treatment of pain, spasticity, and other medical conditions. Implantable infusion device 12 and catheter 14 are implanted by a medical practitioner within the body of patient P during a surgical procedure for conveying infusion media, such as, for example, fluid including intrathecal baclofen for treating the patient.

Catheter 14 is positioned such that the fluid is delivered to patient P through catheter 14 and conveyed to a selected internal delivery location within the body of patient P. Implantable infusion device 12 is implanted such that fluid can be conveyed to a selected internal delivery location, such as, for example, an intrathecal space of a spinal canal associated with vertebrae V. A proximal end of catheter 14 is passed through tissue to the intrathecal space of the spinal canal and coupled to port 20 of implantable infusion device 12. In some embodiments, implantable infusion device 12 is positioned subcutaneously, from approximately 1 centimeter (cm) to 2.5 cm beneath the skin and supported with sutures.

Pump 26 utilizes electromagnetic and mechanical forces to move between a retracted or return stroke position and a forward or pump stroke position to cause the infusion medium to be drawn into and driven out of pump 26 in a controlled manner. In the retracted position, central aperture 46 is substantially filled with infusion media and coil 60 is de-activated, such that the force exerted by coil 60 on piston/pole assembly 30 does not overcome the force of spring 92.

Piston/pole assembly 30 actuates within an enclosure between an interior surface of cover 32 and an exterior surface of barrier plate 62. Spring 92 biases piston/pole assembly 30 away from valve 50 and against protrusions 104 of cover 32. The motion of piston/pole assembly 30 is driven by coil 60. During a pump stroke, current through coil 60 magnetizes magnetic coil housing 70 to attract pole 80. The magnetic attraction force between pole 80 and magnetic coil housing 70 overcomes the force of spring 92 to create a pumping action of piston 48. The motion of piston 48 forces infusion media within central aperture 46 and adjacent to a distal end 106 of piston 48 through one-way valve 50.

Following a pump stroke, current through electromagnetic coil 60 is de-activated, and spring 92 returns piston/pole assembly 30 to its original position against cover 32. As spring 92 moves piston/pole assembly 30, infusion media flows through a gap between piston 48 and the inner surface of sleeve 68 to fill the space within central aperture 46 adjacent to distal end 106 of piston 48. While some infusion media may flow back though the gap between piston 48 and the inner surface of sleeve 68 during a pump stroke, the speed of a pump stroke combined with the viscosity of the therapeutic fluid allows infusion media flowing back though the gap between piston 48 and the inner surface of sleeve 68 during a pump stroke to be negligible.

In some embodiments, the size of the gap between piston 48 and the inner surface of sleeve 68 may be selected according to the fluid being pumped through medical pump 26. In some embodiments, a higher viscosity fluid may take more time than a lower viscosity fluid to flow through the gap between piston 48 and the inner surface of sleeve 68 for a given gap and a given spring force from spring 92. In some embodiments, the size of the gap as well as the spring force from spring 92 may be selected to limit backflow during a pump stroke as well as provide a return stroke for a desired pump stroke rate according to the fluid properties of a particular infusion media to be pumped through medical pump 26. In some embodiments, the gap between piston 48 and the inner surface of sleeve 68 is selected to prevent backflow while spring 92 provides a near minimal spring force to accomplish a return stroke to provide a desired pump stroke rate.

In some embodiments, a pump stoke may include a duration of about 0.01 to 100 milliseconds, whereas a return stroke may include a duration of about 0.5 to 20 seconds. In some embodiments, a pump stoke may include a duration of about 1 to 10 milliseconds, whereas a return stroke may include a duration of about 0.1 to 20 seconds. In some embodiments, a pump stoke may include a duration of about 1 to 5 milliseconds, whereas a return stroke may include a duration of about 0.5 to 5 seconds. In some embodiments, a pump stoke may include a duration of about 3 milliseconds, whereas a return stroke may include a duration of about 2 seconds. In some embodiments, the configuration of piston 48 and sleeve 68 acts as a one-way valve during operation of medical pump 26.

Infusion media driven by piston 48 during a pump stroke is expelled from medical pump 26 through one-way valve 50. One-way valve 50 includes a disc 108, a spring 110 and a bonnet 112. Spring 110 biases disc 108 against seat 66 of sleeve 68. Bonnet 112 maintains spring 110 in place. In some embodiments, bonnet 112 is interference fit to sleeve 68. In some embodiments, bonnet 112 is attached to sleeve 68 using a weld joint and/or screws. In some embodiments, valve 50 is located remotely. In some embodiments, a sealed fluid passageway, such as a catheter, connects sleeve 68 and valve 50. Bonnet 112 includes holes that provide fluid passageways through bonnet 112. When one-way valve 50 is closed, disc 108 seals to seat 66 of sleeve 68. In some embodiments, one-way valve 50 includes a lift check valve. In some embodiments, one-way valve 50 can include ball check valves, diaphragm valves and/or gate valves.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An infusion drive mechanism comprising:
 a housing member including an inner surface that defines a passageway defining a longitudinal axis;
 a coil housing disposed with the housing member and including a coil, the coil housing further including a pole surface;
 a piston defining a first axis and being movable within the passageway to convey at least one infusion medium;
 a pole disposed with the housing member and being connected to the piston, the pole including a pole surface disposed in an electromagnetic flux path with the pole surface of the coil housing, the pole surface of the pole defining at least one cavity disposed adjacent to and non-concentric with the piston; and a biasing member located within the at least one cavity and engaged with the pole surface of the coil housing to orient the first axis transverse relative to the longitudinal axis.

2. An infusion drive mechanism as recited in claim 1, wherein the biasing member engages the pole surface of the coil housing such that a lateral force is applied to the piston.

3. An infusion drive mechanism as recited in claim 1, wherein the biasing member engages the pole surface of the coil housing such that a moment is applied to the piston and the piston is disposed at an angular orientation relative to the passageway.

4. An infusion drive mechanism as recited in claim 1, wherein the biasing member engages the pole surface of the coil housing such that the piston is movable within the passageway substantially independent of orientation of the housing member.

5. An infusion drive mechanism as recited in claim 1, wherein the biasing member includes a coil spring extending between a first end engageable with the pole surface of the pole and a second end engageable with the pole surface of the coil housing.

6. An infusion drive mechanism as recited in claim 1, wherein the housing member is implantable with a body of a patient.

7. An infusion pump comprising:

a pump housing including an inlet, an outlet and an inner surface that defines a chamber disposed in communication with a central bore;

a coil housing disposed with the chamber and including a selectively energizable coil, the coil housing further including a pole surface;

a piston being movable within the central bore between a forward stroke and a return stroke to convey at least one infusion medium;

a pole disposed with the pump housing and being connected to the piston to cause movement of the piston, the pole including a pole surface disposed in an electromagnetic flux path with the pole surface of the coil housing, the pole surface of the pole defining at least one cavity disposed adjacent to and non-concentric with the piston; and a coil spring located within the at least one cavity and engaged with the pole surface of the coil housing to dispose the piston at an angular orientation relative to the central bore.

* * * * *